United States Patent [19]

Castaigne

[11] 4,075,215
[45] Feb. 21, 1978

[54] THIENO-PYRIDINE DERIVATIVES

[75] Inventor: Albert René Joseph Castaigne, Toulouse, France

[73] Assignee: Centre d'Etudes Pour l'Industrie Pharmaceutique, Toulouse, France

[21] Appl. No.: 715,579

[22] Filed: Aug. 18, 1976

Related U.S. Application Data

[62] Division of Ser. No. 660,248, Feb. 20, 1976, which is a division of Ser. No. 435,036, Jan. 21, 1974, abandoned.

[30] Foreign Application Priority Data

Feb. 1, 1973 France .................................. 73.03503

[51] Int. Cl.² ............................................ C07D 417/02
[52] U.S. Cl. ........................ 260/294.8 C; 260/297 B; 424/256
[58] Field of Search .............................. 260/294.8 C

[56] References Cited

U.S. PATENT DOCUMENTS 3,969,358  7/1976  Amselem ....................... 260/294.8 C

FOREIGN PATENT DOCUMENTS 2,404,308  8/1974  Germany ....................... 260/294.8 C Primary Examiner—Alan L. Rotman
Attorney, Agent, or Firm—Young & Thompson

[57] ABSTRACT

Pyridinium derivatives having the formula:

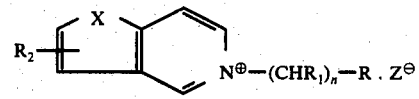

in which X is O or S; R is benzoyl optionally substituted with at least halogen or lower alkyl, lower alkoxy, hydroxy or nitro; $R_1$ is hydrogen, halogen, hydroxy or lower alkyl, $R_2$ is hydrogen or halogen and $n$ is from 1 to 2, and in which $R_1$ may be different in each $CHR_1$ when $n$ is 2.

Said derivatives are therapeutically useful for their antiarrhythmic activity.

5 Claims, No Drawings

THIENO-PYRIDINE DERIVATIVES

This application is a division of my copending application Ser. No. 660,248, filed Feb. 20, 1976, which in turn is a division of my application Ser. No. 435,036, filed Jan. 21, 1974 and now abandoned.

This invention relates to new pyridinium derivatives of the following formula:

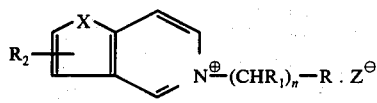
(I)

in which X is oxygen or sulfur; R is benzoyl optionally substituted with 1 to 3 halogen atoms or alkyl groups having 1-6 carbon atoms or alkoxy groups having 1-6 carbon atoms or hydroxy groups or nitro groups; $R_1$ is hydrogen, halogen, hydroxy or alkyl having 1-6 carbon atoms; $R_2$ is hydrogen or halogen and $n$ is an integer from 1 to 2, and in which $R_1$ may have different meanings in each radical $CHR_1$ when $n$ is 2.

Compounds of formula (I) can be prepared by a method comprising condensing a compound of the formula:

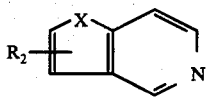
(II)

in which X and $R_2$ having the above meanings, with a halide of the formula $$Z - (CHR_1)_n - R \qquad (III)$$

in which Z is halogen and R, $R_1$ and $n$ have the aforesaid meanings.

The condensation reaction is preferably conducted in a medium comprising an inert solvent, such as acetonitrile, for example.

The starting thieno[3,2-c]pyridines and furo[3,2-c]pyridines having the formula (II) are known compounds which have been described in the literature.

Purification of the products obtained by the process of this invention is preferably effected by extraction with water or an organic solvent.

The pyridinium derivatives of the formula (I) have in particular an anti-arrythmic activity.

The following non limiting examples are given to illustrate the preparation of compounds of this invention.

EXAMPLE 1

Synthesis of 5-phenacyl-thieno[3,2-c]pyridinium bromide (derivative No. 1)

A mixture of thieno[3,2-c]pyridine (13.5 g; 0.10 mole) and phenacyl bromide (19.9 g) (0.10 mole) in acetone (200 ml) is stirred for two hours at room temperature.

The resulting white precipitate is filtered, washed with acetone and dried, to give 29.7 g of crude product in a yield of 89%.

Recrystallisation of the material from water (50 ml) and drying gives 26.6 g (recrystallisation yield: 89.5%) highly hygroscopic white crystals having a melting point (Koefler block) of 206°-207° C.

EXAMPLE 2

Synthesis of 5-(o-methoxy-phenacyl)-thieno[3,2-c]pyridinium bromide (derivative No. 2)

Reaction of thieno[3,2-c]pyridine (13.5 g) with orthomethoxy-phenacyl bromide (21.3 g) according to the procedure of Example 1 gives white crystals (27.34 g) having a melting point (Koefler block) of 258°-260° C.

EXAMPLE 3

Synthesis of 2-chloro-5-phenacyl-thieno[3,2-c]pyridinium bromide (derivative No. 3)

Reaction of 2-chloro-thieno[3,2-c]pyridine (17 g) with phenacyl bromide (20 g) according to the procedure of Example 1 gives white crystals (29.60 g) having a melting point (Koefler block of 239° C.

EXAMPLE 4

Synthesis of N-parachloro-phenacyl-thieno[3,2-c]pyridinium bromide (derivative No. 4)

Reaction of thieno[3,2-c]pyridine (13.5 g) with parachlorophenacyl bromide (22.5 g) according to the procedure of Example 1 gives white crystals (25.80 g) having a melting point (Koefler block) of 208°-210° C.

Using analogous procedures, the following derivatives are obtained:

-derivative No. 5: 5-(3,4-dihydroxy-phenacyl)-thieno[3,2-c]pyridinium chloride (yellowish crystals, m.p. greater than 260° C);

-derivative No. 6: 5-para-fluoro-phenacyl-thieno[3,2-c]pyridinium chloride (white crystals, m.p. 166° C);

-derivative No. 7: N-(para-hydroxy-phenacyl)-thieno[3,2-c]pyridinium chloride (brown powder, m.p. 260° C);

-derivative No. 8: N-(para-methoxy-phenacyl)-thieno[3,2-c]pyridinium bromide (yellowish-white crystals, m.p. greater than 260° C);

-derivative No. 9: N-(meta-methoxy-phenacyl)-thieno[3,2-c]pyridinium bromide (yellow powder; m.p. 240° C).

The results of toxicological and pharmacological tests reported below demonstrate the useful, particularly antiarhythmic, activity of the derivatives of the formula (I).

I. Toxicological investigation

Said investigation demonstrated the low toxicity of the derivatives of the formula (I).

It measured the acute toxicity, the subacute toxicity, the chronic toxicity, the tolerance and the teratology of said derivatives.

For indicative purposes, the $LD_{50}/24$ hrs/kg body weight in mice, by the intravenous route, is 19 mg for derivative No. 1, 18 mg for derivative No. 2, 38 mg of derivative No. 3, 17.5 mg for derivative No. 4, 16 mg for derivative No. 6, 25 mg for derivative No. 7, 32 mg for derivative No. 8 and 16 mg for derivative No. 9.

The subacute and chronic toxicity tests together with the tolerance tests carried out in rats and dogs have shown that the derivatives of the formula (I) were free from any noxious action; indeed, both the biological examinations carried out during the tests and the macroscopic and pathologic study of the animals sacrificed at the end of the experiments failed to disclose any anomaly in the treated animals.

The teratologic investigation was carried out in mice, rats and rabbits. It showed that the derivatives of the formula (I) were free from any effect on the fecundation and the gestation of the female animals and produced no modifications of the morphological appearance of the young born during such experimentation.

II. Pharmacological investigation

The derivatives of the formula (I) possess important anti-arrhythmic properties.

The tests carried out in rabbits and dogs, according to the method of Schmitt H. and H. Schmitt [Arch. Int. Pharmacodyn., 1960, 127 (1, 2)], have shown that at an oral dosage of 5 mg/kg said derivatives protected completely the test animals against arrhythmia induced by barium chloride administration.

There are no regular or dispersed extrasystole bursts in the protected animals.

The same inhibition is also found with respect to other arrhythmia-producing agents such as calcium chloride, K-strophantine, aconitine, isoprenaline, adrenaline and ouabaine.

The anti-arrhythmic properties of the compounds of the formula (I) were also investigated by a different method. Rhythm disorders were produced in dogs by ligation of a coronary artery.

It was shown that administration of a derivative of the formula (I) was capable of restoring the sinus rhythm and of improving the perturbed electric activity of the heart by causing a reappearance of a rhythmic ventricular activity.

The toxicological and pharmacological investigations reported above demonstrate the good tolerance of the compounds of the formula (I) and their outstanding anti-arrhythmic action.

Therapeutic compositions containing a derivative of the formula (I) may be formulated for oral administration as tablets, coated tablets, capsules and drops. They may also be formulated as suppositories for rectal administration and as injectable ampoules for parenteral administration.

Each unit dose contains advantageously from 0.005 to 0.100 g of a derivative of the formula (I) together with therapeutically compatible excipients, the daily dosage regimen varying within a range from 0.005 g to 0.300 g.

Non limiting examples of pharmaceutical formulations of the above composition are given below.

| EXAMPLE 10 - | Coated tablets | |
|---|---|---|
| Core | Derivative No. 1 | 0.025 g |
| | Talc | 0.010 g |
| | Lactose | 0.005 g |
| | Magnesium stearate | 0.005 g |
| | Kaolin | 0.003 g |
| | Starch | 0.005 g |
| | Titanium dioxide | 0.002 g |
| Coating | Starch | 0.010 g |
| | Gum arabic | 0.005 g |
| | White shellac | 0.001 g |
| | White wax | 0.002 g |
| | Sugar syrup sufficient to make 1 coated tablet | |
| EXAMPLE 11 - | Tablets | |
| | Derivative No. 6 | 0.075 g |
| | Magnesium hydrocarbonate | 0.020 g |
| | Corn starch | 0.010 g |
| | Calcium carboxymethyl cellulose | 0.005 g |
| | Magnesium stearate | 0.003 g |
| | Stearic acid | 0.003 g |
| | Talc | 0.003 g |
| EXAMPLE 12 - | CAPSULES | |
| | Derivative No. 3 | 0.100 g |
| | Wheat starch | 0.025 g |
| | Talc | 0.010 g |
| | Lactose | 0.010 g |
| EXAMPLE 13 - | Drops | |
| | Derivative No. 7 | 5.00 g |
| | Flavored excipient, sufficient for | 100 ml |
| EXAMPLE 14 - | Suppositories | |
| | Derivative No. 1 | 0.025 g |
| | Semi-synthetic triglycerides, sufficient to make | 1 suppository |
| EXAMPLE 15 - | Injectable ampoules | |
| | Derivative No. 1 | 0.010 g |
| | Isotonic solvent, sufficient to make | 3 ml |

In view of their anti-arrhythmic action, the derivatives of the formula (I) are usefully applicable therapeutically whenever it is desired to obtain an anti-arrhythmic action either on a healthy heart or on rhythm disorders subsequent to a previous infarction. They exhibit good clinical and biological tolerance, in view of the fact that no signs of blood, renal or liver toxicity could be detected by the routine examinations effected on the patients undergoing treatment.

They are applicable in cardiology in cases of ventricular tachycardia, of venticular extrasystoles, and in disorders of the cardiac rhythm due to post-digitalization myocardial hyperexcitability. They are also anesthesiologically applicable in the preparation for heart surgery, and for general surgery in old people.

Having now described my invention what I claim as new and desire to secure by Letters Patent is:

1. A compound selected from the group consisting of 5-phenacyl-thieno[3,2-c]pyridinium bromide, 5-(o-methoxy-phenacyl)-thieno[3,2-c]pyridinium bromide, 2-chloro-5-phenacyl-thieno[3,2-c]pyridinium bromide, N-parachlorophenacyl-thieno[3,2-c]pyridinium bromide, 5-(3,4-dihydroxyphenacyl)-thieno[3,2-c]pyridinium chloride, 5-para-fluorophenacyl-thieno[3,2-c]pyridinium chloride, N-(para-hydroxyphenacyl)-thieno[3,2-c]pyridinium chloride, N-(para-methoxyphenacyl)-thieno[3,2-c]pyridinium bromide and N-(meta-methoxyphenacyl)-thieno[3,2-c]pyridinium bromide.

2. 5-phenacyl-thieno[3,2-c]pyridinium bromide.

3. 5-(o-methoxy-phenacyl)-thieno[3,2-c]pyridinium bromide.

4. 2-chloro-5-phenacyl-thieno[3,2-c]pyridinium bromide.

5. N-parachloro-phenacyl-thieno[3,2-c]pyridinium bromide.

* * * * *